| United States Patent [19] | [11] | 4,148,871 |
|---|---|---|
| Pitt et al. | [45] | Apr. 10, 1979 |

[54] SUSTAINED SUBDERMAL DELIVERY OF DRUGS USING POLY(ε-CAPROLACTONE) AND ITS COPOLYMERS

[76] Inventors: Colin G. Pitt; Anton E. Schindler, both of RTI, P. O. Box 12194, Research Triangle Park, N.C. 27709

[21] Appl. No.: 840,989

[22] Filed: Oct. 11, 1977

[51] Int. Cl.² .................. A61K 31/74; A61K 9/52
[52] U.S. Cl. ................... 424/19; 128/260; 424/21; 424/22
[58] Field of Search .................. 424/14–22, 424/78; 128/260, 335.5; 260/78.3 R, 78.3 UA

[56] References Cited

U.S. PATENT DOCUMENTS

| 2,890,208 | 6/1959 | Young et al. | 260/878 R |
| 3,021,309 | 2/1962 | Cox | 260/78.3 R |
| 3,773,919 | 11/1973 | Boswell et al. | 424/19 |
| 3,887,699 | 6/1975 | Yolles | 424/19 |
| 3,991,766 | 11/1976 | Schmitt et al. | 424/19 X |

*Primary Examiner*—Shep K. Rose
*Attorney, Agent, or Firm*—Holman & Stern

[57] ABSTRACT

Compositions containing either poly(ε-caprolactone) or copolymers of ε-caprolactone with other lactones, together with a drug, when subdermally implanted in the body, provide a slow sustained release of the drug. The polymers may be designed to biodegrade during or subsequent to the depletion of the drug.

15 Claims, 2 Drawing Figures

SUSTAINED SUBDERMAL DELIVERY OF DRUGS USING POLY(ε-CAPROLACTONE) AND ITS COPOLYMERS

BACKGROUND AND SUMMARY OF THE INVENTION

The invention described herein was made the course of work under a grant or award from the Department of Health, Education and Welfare.

The present invention relates to novel polymer-drug formulations and their use in bringing about desired biological effects when applied subdermally to living organisms, particularly human beings and warm-blooded animals such as farm and domestic animals and pets.

U.S. Pat. No. 3,887,699 to Yolles discloses an article for dispensing drugs formed from a biodegradable polymeric material which is shown as being a polylactide. The polylactides form copolymers with comonomers such as glycolide and pivalolactone as well as cyclic esters of various α-hydroxy carboxylic acid. U.S. Pat. No. 3,736,646 to Schmitt et al. discloses similar compositions. Neither of these references, however, discloses the use of the ε-hydroxy carboxylic lactones.

U.S. Pat. Nos. 2,890,208 and 3,021,309 disclose the preparation of polyesters, such as poly (ε-caprolactone) and copolymers of ε-caprolactone with other lactones, by polymerization of cyclic esters in the presence of various metal compounds. These patents do not, however, disclose the concept of a polymer-drug formulation for the sustained subdermal delivery of drugs.

By the present invention, there is provided a nonirritating pharmaceutical composition for subdermal administration, designed to release effective amounts of a drug over a pre-determined period of time. The composition includes either poly(ε-caprolactone) or a copolymer of ε-caprolactone with other lactones. The drug may be either intimately mixed with the polymer composition, or contained within the cavity of a hollow device constructed from the polymer. The shape of these polymeric devices may be a cylinder, sphere, slab, or any other common geometric form. When the drug is intimately mixed with the polymer or copolymer, the proportion of the drug may range from 0.01% by weight of drug and 99.9% by weight of polymer or copolymer to 90% by weight of drug and 10% by weight of polymer or copolymer. When the drug is contained within the cavity of the polymer device, it may be present as a solid, preferably micronized, powder or mixed with a suitable solvent, diluent, or dispersing agent. When the invention is applied subdermally, using either minor surgery or trocar injection, it has the property of releasing pre-determined amounts of the drug or drugs over a predetermined period of time.

Furthermore, the polymers have the valuable characteristic undergoing gradual hydrolysis to low molecular weight materials, which are then metabolized and eliminated from the body. The rate of biodegradation of the polymer may be controlled by proper choice of the chemical structure and its molecular weight such that dissolution of the polymer by the body may either take place while the drug is being released or subsequent to release of all of the drug. The polymers are non-toxic and biodegrade to non-toxic materials. The use of the present invention has been found to result in no inflammation, irritation or edema at the implantation sites.

The polymer-drug composite, when implanted subdermally, provides a convenient formulation for controlled drug administration which requires no attention or motivation on the part of the user, is capable of delivering the drug at therapeutic levels for periods of up to at least one year, and need not be removed surgically after its useful lifetime.

As used herein, the term "drug" is intended in its broadest sense as defined in the Federal Food, Drug and Cosmetic Act, Section 201(2) g to include:
1. Articles recognized in the official United States Pharmacopoeia, official Homeopathic Pharmacopoeia of the United states, or official National Formulary, or any supplement of any of them;
2. Articles intended for use in the diagnosis, cure, mitigation, treatment, or prevention of disease in man or other animals;
3. Articles (other than food) intended to affect the structure or any function of the body of man or other animals; and
4. Articles intended for use as a component of any article specified in clause 1, 2 or 3; but does not include devices or their components, parts or accessories.

Classes of drugs that may be specifically mentioned include: contraceptive agents, such agents being either steroidal or non-steroidal; male and female hormones; narcotics and narcotic antagonists; anti-neoplastic agents; and antiinflammatory agents.

The polymers which are employed in the compositions of the present invention comprise repeating units of the formula:

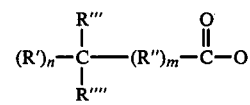

wherein R' and R" are lower alkylenes of up to six carbon atoms; n and m are 0 or 1; and R''' and R'''' are hydrogen or lower alkyl groups containing from 1 to about 6 carbon atoms. In the case where R''' and R'''' are different, the unit can exist in optically active (D- and L-) forms or as DL-racemic mixture.

Illustrative of the monomers which can be employed to form such homopolymers and copolymers useful in preparing the formulations of this invention are: glycolide, dilactide, pivalolactone, valerolactone, ε-caprolactone, ε-heptalactone, and ε-decalactone. The preferred sole monomer or principal monomer is ε-caprolactone. Thus, in the formula above, preferably at least 5% by weight of the polymer is formed of the repeating unit

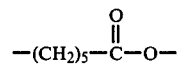

derived from ε-hydroxy caproic acid, wherein m=0, n=1, R'=(CH$_2$)$_4$ and R''' and R''''=H.

In an alternative composition, at least 5% by weight of the polymer may be formed of the repeating unit

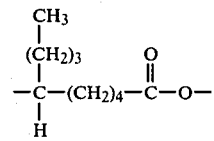

derived from ε-hydroxydecanoic acid, wherein m=1, n=0, R''=(CH₂)₄, R'''=(CH₂)₃CH₃ and R''''=H.

In another alternative composition, at least 5% by weight of the polymer may be formed of the repeating unit

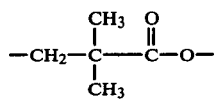

derived from β-hydroxypivalic acid, wherein n=1, m=0, R'=CH₂, and R''' and R''''=CH₃.

In preparing the polymers and copolymers from which the formulations of the present invention are made, the appropriate intermolecular cyclic esters or intramolecular cyclic esters of the hydroxy acids are employed. Intermolecular cyclic esters containing six membered rings, e.g., glycolide, are usefuly employed to introduced repeating units derived form α-hydroxy acids. Monomeric lactones, for example ε-caprolactone, are usefully employed to introduce repeating units derived from other hydroxy acids.

The polymerization is effected, as is known in the art, by heating the lactide or lactone, or mixture of the two, at a temperature between 100 and 200° C., in the presence of a metal oxide or compound thereof, under anhydrous conditions in an inert atmosphere. Specifically useful catalysts include diethyl zinc, stannous octoate, stannous chloride, and diethylaluminum chloride. The amount and type of catalyst used determine the particular temperature and time required to produce polymers useful for conversion to the formulations of this invention. The amount of catalyst can be as low as $3 \times 10^{-4}$ weight percent or as high as 2.3 weight percent of the total weight of reactants. As a rule, the lower the temperature and the amount of catalyst, the lower the amount of conversion of monomer to polymer in a given time period.

Th following is a generalized description of the method for preparing polymers or copolymers useful in the formulations of the present invention.

Polymerizations are carried out in bulk or in the presence of a inert diluent, under a dry, inert atmosphere, e.g., nitrogen, using freshly recrystallized or distilled monomers. Polymerization vessels of appropriate size are charged with the monomers and the proper amount of a catalyst. After degassing the reaction mixture, the vesseis are sealed and heated at an elevated temperature for a time period required to accomplish the desired conversion. The degree of conversion obtained is critical for the preparation of copolymers of even composition.

The thus obtained polymers are freed of unchanged monomer and catalyst residue by dissolving the reaction mixture in a suitable solvent, e.g., methylene chloride or acetone, and precipitating the polymer by adding these solutions to a larger volume of stirred methanol. The freshly precipitated polymers are immediately washed free of methanol with water using vigorous agitation. The filtered polymers are predried in vacuo at ambient temperature and then at 70° C.

The drug and the polymer composition may be formulated by any of a number of conventional methods well known to those skilled in the art. In the case of formulations involving intimate mixtures of polymer and drug, the desired proportions of the components are dissolved in a common solvent such as methylene chloride or chloroform. To prepare a film or slab, the solution may be cast on clean glass plates and spread with an adjustable Boston-Bradley applicator set at the desired clearance. After the films are touch dry, the residual solvent is removed in vacuo at room temperature. The films are then released from the plate by floating in water. This technique provides films with thicknesses up to 60 microns. Thicker films are prepared by compression molding of a powdered mixture of the drug and polymer in a heated hydraulic press. The press temperature employed (100°–200° C.) depends on the molecular weight and melt viscosity of the polymer, and film thickness may be controlled by spacers. To facilitate release of the films from the press, the polymer is molded between mylar sheets or polypropylene sheets. Compression molding may be equally as well employed to obtain other geometric forms. Extrusion of the powdered polymer-drug mixture from a heated die is used to obtain solid rods. Here too, the temperature of the die is determined by the melt viscosity of the polymer.

BRIEF DESCRIPTION OF THE DRAWINGS

The advantages and features of the present invention will be more fully understood from the following description of the preferred embodiments taken in conjunction with the accompanying drawings, wherein.

DESCRIPTION OF THE PREFERRED EMBODIMENTS

The preparation of formulations in which the drug is contained within the cavity of the polymeric device of the present invention is a two step process. The first step involves preparation of the drug-free polymeric device. This is accomplished by conventional methods, such as compression molding, melt coating, annealing rolled films, or extrusion. The drug may be introduced into the cavity of such devices as a micronized powder, or as a mixture with a suitable solvent, diluent or dispersing agent. It is desirable that the amount of drug present be such that at least some of it is retained in the solid form. As is known to those skilled in the art, this will have the effect of producing a constant rate of release of the drugs from the polymer device. The nature of the solvent, diluent or dispersing agent should be such that it does not dissolve the polymer to any appreciable extent, but that the rate of diffusion of the drugs through it be very rapid compared with diffusion through the polymer. Examples of suitable solvents, diluents, and dispersing agents include sesame oil, mineral oil, various commercial preparations such as carboxymethyl cellulose sorbitan trioleate, and sorbitan stearate, as well as low molecular weight polymers or oligomers including polyethers and polyesters.

Figure 1:
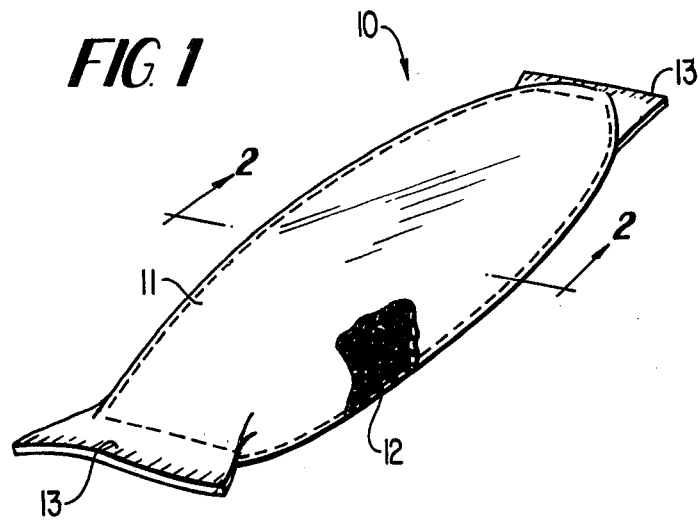
FIG. 1 is a perspective view of a device prepared in accordance with the present invention.
Figure 2:
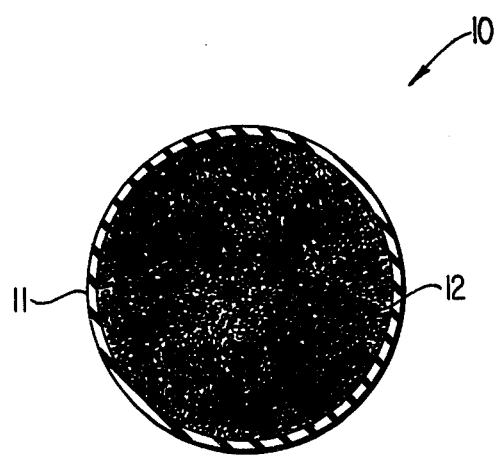
FIG. 2 is a cross-sectional view taken along line 2—2 of FIG. 1.

As is well documented in the public literature, and as well known to those skilled in the art, the amount of drug, the dimensions of the polymeric device, and the amount of diluent, solvent or dispersing agent, may be varied such that the rate of the drug delivery and the time over which the drug is delivered are considered optimum for the particular therapeutic application. In the device of the present invention as shown in FIGS. 1 and 2, the device is in the form of a cylindrical tube having walls 11, and with the drug 12 contained within the interior cavity formed by the walls 11, the drug 12 being in the form of a micronized powder.

The polymeric devices 10 of the present invention containing drug filled cavities may be sealed by application of further amounts of molten polymer to the device, or by bringing the surfaces of the device together and applying mild heat. Thus in FIG. 1, the end portions 13 of the tubular walls 11 are shown as having been brought together and sealed by the application of mild heat.

The rate at which the device is degraded within the body is determined by the chemical structure and the molecular weight of the polymer which is chosen for fabrication of the device. If poly (ε-caprolactone) with a molecular weight corresponding to an intrinsic viscosity of greater than one dl/g in benzene used, the polymer undergoes a continued slow decrease in molecular weight after subdermal implantation, but does not begin to lose significant mechanical strength or weight for at least 12 months. A copolymer of caprolactone and DL-lactic acid with the same viscosity is degraded within two to three months; a copolymer of caprolactone and ε-decalactone shows intermediate behavior. Radiation or peroxide-induced crosslinking of said polyers serves to increase their biostability. If it is desired for particular applications to have a shorter effective life a molecular weight corresponding to an intrinsic viscosity of less than one dl/g, for eximple, down to about 0.4,dl/g, may be chosen. Likewise, longer effective life may be obtained by utilizing a polymer having a higher viscosity, up to about 2-3 dl/g.

The following examples illustrate the products and process of the present invention. All parts are by weight unless stated otherwise.

EXAMPLE 1

Poly (caprolactone), with an intrinsic viscosity in benzene of 1.47 dl/g, was prepared from ε-caprolactone according to the general procedure described above. Tubes of this polymer, internal diameter 1.23 mm and external diameter 1.89m, and length 2 cm, were filled with a slurry of micronized, tritium labeled Norethindrone (1 part) and sesame oil (3 parts). The tube ends were then heat sealed. Replicate tubes were subdermally inserted in the dorsal region of rabbits, and the amount of Norethindrone release from tubes was determined daily by measurement of the total radioactivity present in the urine and feces. A release rate of 25 μg per day per centimeter tube length was observed for more than 250 days.

Tubes were perodically removed and the properties of the polymer evaluated. After 4 months, the intrinsic viscosity of the polymer in benzene had decreased to 1.00 dl/g; after 16 months this value was 0.4 dl/g. The polymer tubes had lost less than 5% of their weight after 16 months, but after 20 months were fragmented and had lost 20% of their weight. After 30 months, none of the polymer tubes could be detected at the implant sites.

EXAMPLE 2

Poly (ε-caprolactone-co-DL-lactic acid) was prepared by copolymerization of ε-caprolactone (614 parts) and DL-dilactide (386 parts) in the presence of stannous octoate (0.15 parts) at 150° C. for 86 hours, according to the general procedure described above. After precipitation, the polymer was a white powder with an intrinsic viscosity in benzene of 1.79 dl/g. Nuclear magnetic resonance analysis established that the polymer was composed of 25% of lactic ester units and 75% of caproic ester units.

Tubes of this copolymer, internal diameter 1.25 mm and external diameter 1.9 mm, and length 2 cm, were filled with micronized testosterone which had been labeled with tritium. Tube ends were heat sealed. Replicate tubes were inserted into the dorsal region of rabbits and the daily amount of testosterone released from the polymer capsules was determined by measurement of the total radioactivity present in urine and feces. In replicate experiments a release rate of 35 μg per day per centimeter tube length was observed for at least 100 days.

Tubes of the same copolymer, diameter 1.25 mm and external diameter 1.9 mm, and length 2 cm, were filled with a slurry of 1 part of tritium labeled micronized testosterone propionate and 3 parts of sesame oil, and the tube ends were heat sealed. Each tube was subcutaneously implanted in the dorsal region of a rabbit, and the daily amount of testosterone propionate released from the tube was determined by measurement of the radioactivity present in the urine and feces. The daily release rate was 40 μg per centimeter tube length, and this rate was sustained for a period of at least 60 days.

Periodic removal of tubes from the implant sites showed that the intrinsic viscosity of the polymer decreased with time. Tubes removed after 120 days were fragmented; after 200 days no polymer remained at the implant sites.

It is thought that the invention and many of its attendant advantages will be understood from the foregoing description, and it will be apparent that various changes may be made in the compositions and methods described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. A subdermally implantable pharmaceutical composition comprising
   (a) a surgically implantable device in the form of a macrocapsule having a hollow cavity and being composed of a polymer or copolymer having repeating units of the formula

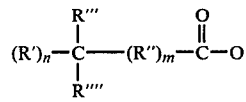

wherein R' and R" are lower alkylene groups of up to six carbon atoms; n and are 0 or 1; and R''' and R'''' are either hydrogen or a lower alkyl group of from 1 to about 6 carbon atoms; at least 5% of the polymer or copolymer being formed of the repeating unit

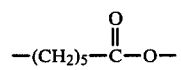

derived from ε-hydroxy caproic acid, where m=0, n=1, R'=(CH₂)₄, and R''' and R''''=H, and
   (b) a drug contained within the hollow cavity of said device; said device, composed of said polymer or copolymer, having a sufficiently high permeability to the drug to enable it to be used in said macrocapsule form for subdermal implantation, being capable of holding a high drug content which can be released in an effective amount at a sustained constant rate for a long time, and which is capable of biodegrading after the drug supply has become depleted.

2. The pharmaceutical composition of claim 1, wherein said polymer comprises poly(ε-caprolactone) with a molecular weight corresponding to an intrinsic viscosity of greater than 1 dl/g in benzene.

3. The composition of claim 1 in which the device and the drug are present in the composition in the ratio of 10% to 90% respectively.

4. The pharmaceutical composition of claim 1 in which the drug is a steroidal contraceptive agent.

5. The pharmaceutical composition of claim 1 in which the drug is a non-steroidal contraceptive agent.

6. The pharmaceutical composition of claim 1 in which the drug is a narcotic.

7. The pharmaceutical composition of claim 1 in which the drug is a narcotic antagonist.

8. The pharmaceutical composition of claim 1 in which the drug is a hormonal agent.

9. The pharmaceutical composition of claim 1 in which the drug is an anti-neoplastic agent.

10. The composition of claim 1 in which the drug release can be sustained for a period of time of up to at least one year.

11. The pharmaceutical composition of claim 1 in which the polymer is a homopolymer of ε-caprolactone.

12. The pharmaceutical composition of claim 1 in which the copolymer consists of ε-caprolactone as the principal monomer and the co-monomer is a member selected from the group consisting of glycolide, dilactide, pivalolactone, valerolactone, ε-heptalactone, and ε-decalactone.

13. The pharmaceutical composition of claim 1 in which the drug, contained within the cavity of the device, is present as a solid micronized powder.

14. The pharmaceutical composition of claim 1 in which the drug, contained within the cavity of the device, is present as a solid micronized powder mixed with a suitable solvent, diluent, or dispersing agent.

15. A surgically implantable pharmaceutical composition comprising an intimate mixture of a drug and a polymer or copolymer having repeating units of the formula

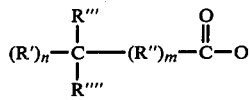

wherein R' and R'' are lower alkylene groups of up to mix carbon atoms; n and m are 0 or 1; and R''' and R'''' are either hydrogen or a lower alkyl group of from 1 to about 6 carbon atoms; at least 5% of the polymer or copolymer being formed of the repeating unit

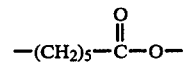

derived from ε-hydroxy caproic acid, where m=0, n=1, R'=(CH$_2$)$_4$, and R''' and R''''=H.

* * * * *